United States Patent [19]

Solari

[11] 4,367,561

[45] Jan. 11, 1983

[54] SAFETY SPORT GOGGLES

[76] Inventor: Ray L. Solari, 1670 Cordova St., Los Angeles, Calif. 90007

[21] Appl. No.: 838,809

[22] Filed: Oct. 3, 1977

[51] Int. Cl.3 .......... A61F 9/02

[52] U.S. Cl. .......... 2/439; 2/9

[58] Field of Search .......... 2/431, 433, 439, 9, 2/10

[56] References Cited

U.S. PATENT DOCUMENTS 924,613 6/1909 Hellawell .......... 2/9

1,336,009 4/1920 Wilmer .......... 2/431

1,523,521 1/1925 Goodman .......... 2/9

3,373,443 3/1968 Marietta .......... 2/9

FOREIGN PATENT DOCUMENTS 622302 4/1949 United Kingdom .......... 2/433

*Primary Examiner*—Peter P. Nerbun

*Attorney, Agent, or Firm*—George J. Netter

[57] ABSTRACT

The described sport goggles have frames which fit closely about the temples and across the nose, and include enlarged viewing openings with relatively narrow members extending from the top and lower parts of the frame inwardly toward each other in the frame viewing openings. These frame members prevent a ball, racquet, hand or other items from contacting the eye or immediately adjacent parts of the head and face. In a further version where the game ball is relatively small, that part of the frame defining the viewing openings immediately adjacent the nose extends horizontally into the viewing opening, which further restricts the area of the viewing opening and yet does not interfere with the visibility of the player during participation in the sport. An adjustable nose-piece permits precise fitting of the goggles to the wearer's face.

1 Claim, 6 Drawing Figures

21'
10
22
24
26
25
23
21

SAFETY SPORT GOGGLES

The present invention relates generally to safety sport goggles, and, more particularly, to goggles especially for use in sporting activities to prevent injury to a player from a ball, equipment, hands, or the like.

FIELD AND BACKGROUND OF THE INVENTION

In a large number of sporting activities, such as tennis, handball, squash, racquet ball, basketball, soccer, and other sporting activities in which there is fast movement of the players and the use of a ball, there is the continuing danger of a participant being struck in the eye by the ball, racquet or hand of an opponent, which can result in severe injury or even, in some cases, in loss of an eye. It is, therefore, clear that the use of some means for protecting the eyes of a player from injury is advisable.

An excellent form of safety goggles are those disclosed in copending U.S. Pat. application Ser. No. 790,479, now U.S. Pat. No. 4,229,837, SAFETY GOGGLES, by R. L. Solari, in which portions of the goggle frame have specially shaped openings providing good visibility, but preventing balls, equipment or the like from contacting the eye. The goggles disclosed in the copending application are a substantial improvement over known prior art goggles or glasses which have included transparent means of a non-breakable character and have been found either cumbersome to wear or have restricted the visibility of the wearer to the point of interfering with the performance of the sport.

SUMMARY OF THE INVENTION

Sport goggles constructed in accordance with the present invention have frames which are adapted to fit closely about the temples and across the nose, and include enlarged viewing openings with relatively narrow members from the top part of the frame and from the lower part of the frame which extend inwardly toward each other in the frame viewing openings. These frame members serve as obstructions to prevent a ball, racquet, hand or other items from contacting the eye or immediately adjacent parts of the head and face.

In a further version that is particularly useful where the game ball is relatively small, such as in squash or handball, for example, that part of the frame defining the viewing openings immediately adjacent the nose extends horizontally into the viewing opening, which further restricts the area of the viewing opening and yet does not interfere with the visibility of the player during participation in the sport. At the outermost end of each viewing opening at the frame portion that extends over the temples of the player, there is a projection from the frame wall back into the viewing opening which prevents, say, a ball coming in from the side and impinging onto the eye. An adjustable nose-piece permits precise fitting of the goggles to the wearer's face.

DESCRIPTION OF PREFERRED EMBODIMENTS

Before turning to the details of the construction of the safety sport goggles of this invention, a few introductory comments may be useful. First of all, it is clear that for maximum visibility, safety goggles to be used in a sport cannot utilize anything which completely covers the eyes (e.g., a transparent plastic shield), since even when new these can always be detected by the eye, and after some use become increasingly less transparent, due to scratches which develop from contact during participation in the sport or from contacting metal parts, for example, when stored in a locker. It has also been found that to merely haphazardly locate obstructions which extend into the goggle eye space can result in considerable interferences with vision, even though the obstruction may be relatively small. For example, a horizontal band extending in both directions from a point directly in front of the eye must be kept completely free of obstructions for some distance, since otherwise there is substantial interference with the peripheral or retoral vision of the wearer which is very important in a game such as handball, squash, tennis or the like. On the other hand, the region closely adjacent the nose can include an obstruction and yet not interfere with the vision of the wearer in any significant amount. Directly in front of the eye or slightly to the side can also include vertically extending obstructions, and particularly the regions below the eye, since they are not used to any significant extent in either direct or peripheral vision. The shape of the frame obstructions must be kept simple, for if too complex in appearance they will constantly catch the eye and attract attention to the obstruction, which, of course, distracts and breaks the concentration of the wearer, thereby impairing performance in the sport.

Figure 1:
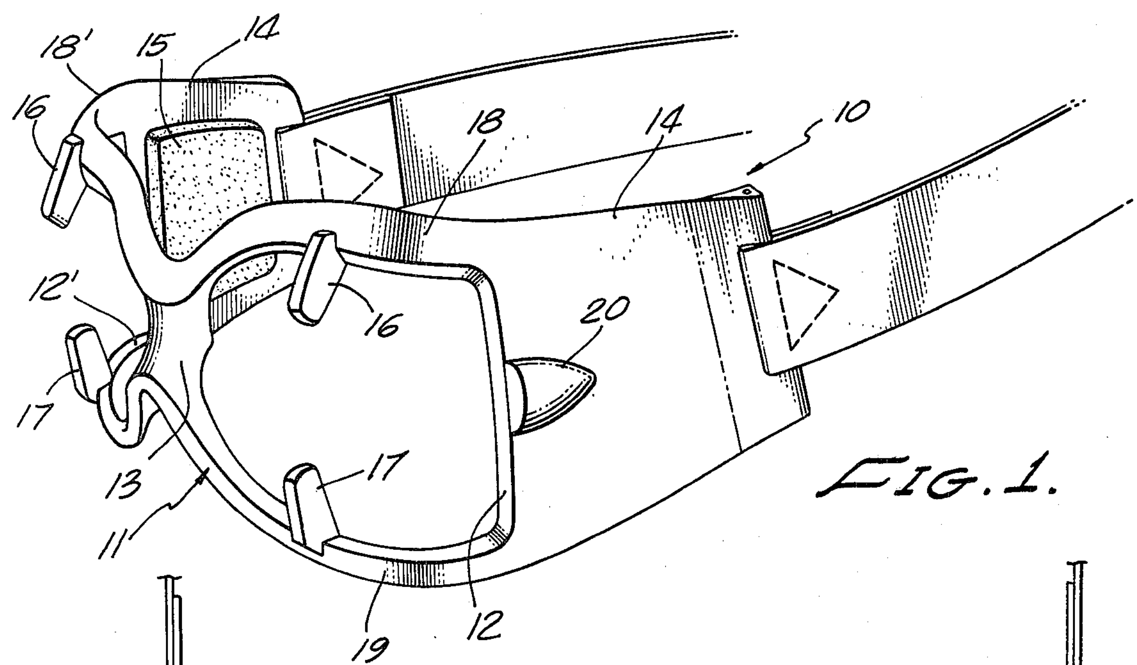
FIG. 1 is a perspective view of a first embodiment of safety goggles in accordance with this invention.
Figure 2:
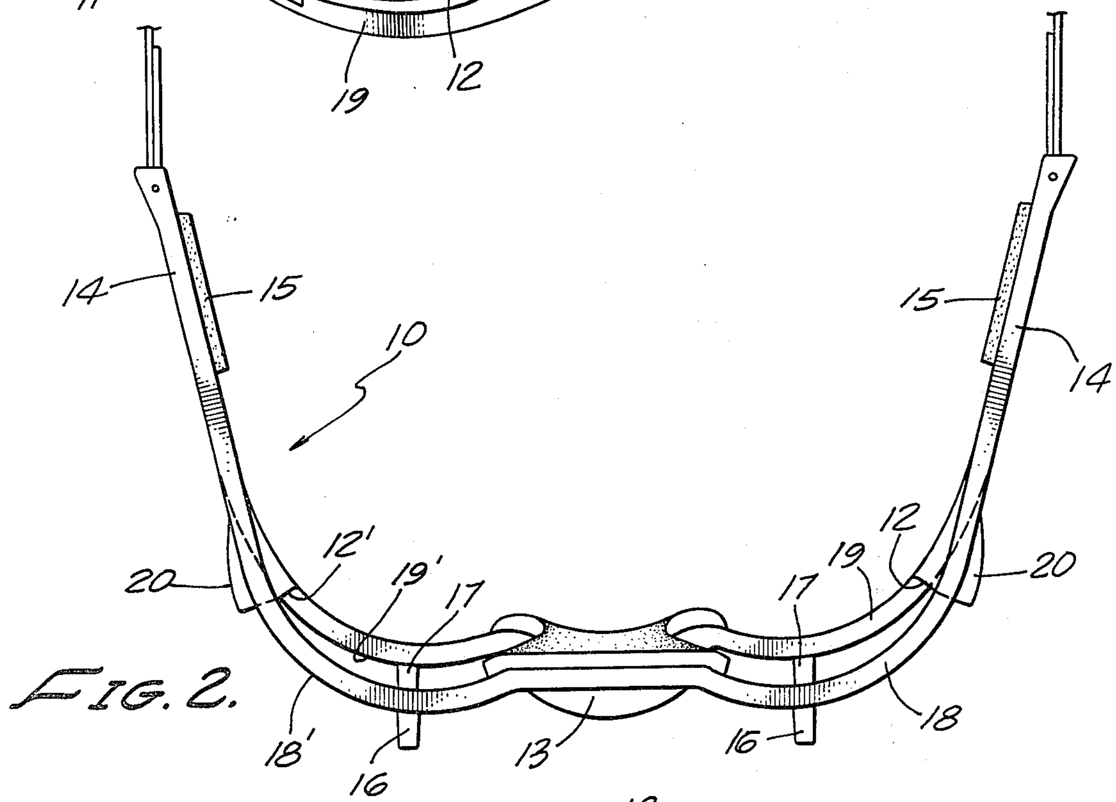
FIG. 2 is a top plan view of the goggles of FIG. 1.
Figure 3:
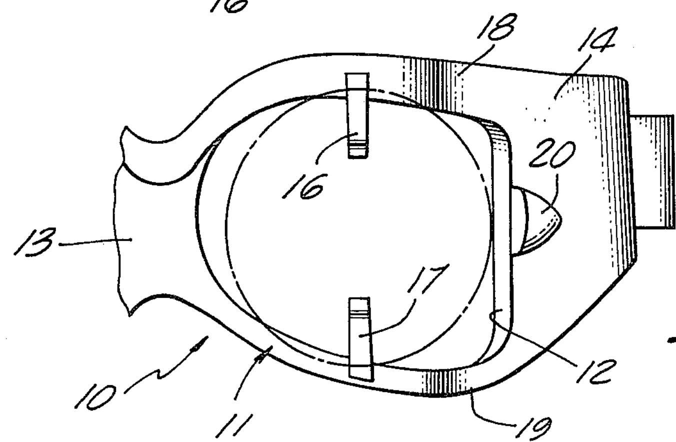
FIG. 3 is a front elevational, partially fragmentary view of the goggles of FIGS. 1 and 2.

Turning now to the drawing, and with reference particularly to FIGS. 1–3, one form of this invention is the goggles shown enumerated generally as at 10, and which has especial utility in protecting the wearer during tennis. In the major aspects, the goggles are seen to include a one-piece frame 11 formed into a generally U-shape for receipt onto the face of the wearer over his eyes and extending onto each temple. The goggle frame has a pair of enlarged, horizontally extending viewing openings 12 and 12', one for each eye, each of which openings is rounded immediately adjacent the nose-piece 13 and terminates at an outermost end in a relatively vertical end wall which coincides substantially with the edge of the eye socket. The frames also include, outwardly of the openings 12 and 12', imperforate parts 14 which extend immediately opposite and substantially covering the temples of the individual. On the inner surface of the temple frame parts 14, there are provided soft resilient cushioning pads 15 which contact the sides of the head, and, more particularly, the temples of the wearer to protect that part of the wear's head.

A pair of relatively narrow obstruction members 16 and 17 extend into each of the viewing openings 12 and 12' from the top and bottom of the frame, respectively. These obstructions lie substantially along a vertical line directly in front of the forward looking eye and define a space between their outermost ends that is substantially less than the diameter of a tennis ball. It is important that the maximum open spacing between frame parts be maintained throughout the entire area of the eye openings, since a hard hit tennis ball compresses somewhat, allowing a part thereof to extend farther inwardly toward the eye than does a softer hit ball.

The obstruction members 16 and 17 also are canted so that their outermost ends extend outwardly away from the goggle frames. By this construction, the members 16 and 17 are considerably strengthened against breakage from contact with a tennis ball, racquet or the like.

By comparison of FIGS. 1 and 2, it will be noted that the goggles, by virtue of the angularly disposed members 16 and 17, the upper and lower rounded frame portions 18, 18' and 19, 19', and the thickened or raised frame parts 20, that a corresponding plurality of deflection points are provided. The purpose of the deflection points is to cause a ball or the like impinging upon the goggles in the eye region to be deflected and therefore not transfer its entire kinetic force to the goggles. Thus, for a ball coming straight into the front of the goggles, not only do the members 16 and 17 prevent access to the eyes, but they also deflect the ball upwardly or downwardly, as the case may be.

Figure 4:
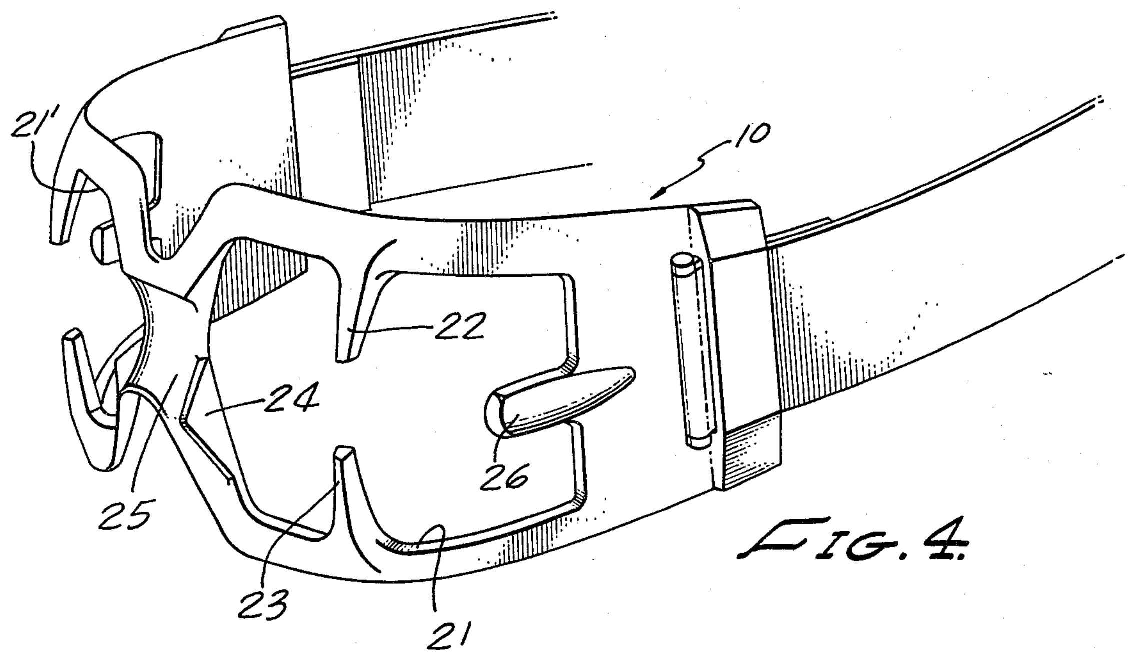
FIG. 4 is a perspective view of a further embodiment of the invention for use in a sport having a relatively small game ball.
Figure 5:
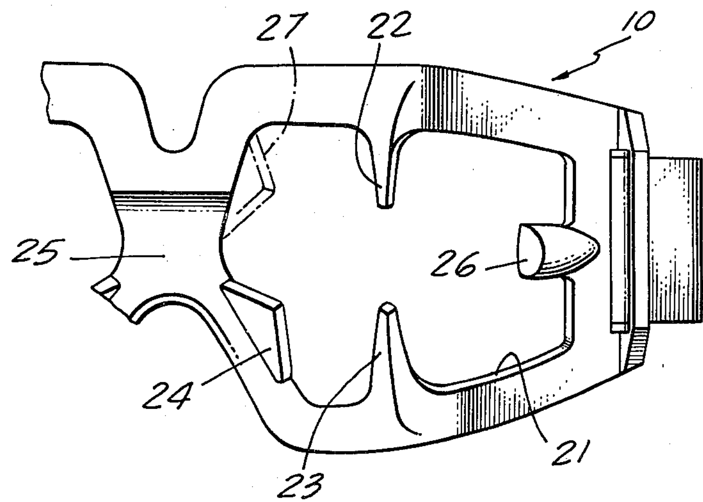
FIG. 5 is a front elevational, partially fragmentary view of the sport goggles of FIG. 4.

Turning now to FIGS. 4 and 5, there is shown a further embodiment of the invention especially advantageous for use in such games as handball, racquet ball and squash, where the ball is smaller than a tennis ball. In this case, the goggle frames are constructed generally as in the first described embodiment with frame openings 21, 21' substantially identical in overall dimensions to openings 12, 12' of the first described embodiment. A pair of relatively narrow obstruction members 22 and 23, integral with the frames, extend into the openings 21, 21' from the upper and lower frame parts, respectively. These obstructions lie just outwardly (i.e., toward the temples) of the normal forward-looking position of the eyes. A further member 24, of generally triangular shape and integral with the goggle frame nose-piece 25, extends both into the frame opening and outwardly therefrom at a point below the normal eye level. The members 22, 23 and 24 are so located that the open distance is less than the diameter of the smallest ball of the sport concerned (e.g., squash).

Outwardly of the members 22 and 23 (i.e., toward the temples) a further obstruction member 26, integral with the frame, extends along the horizontal axis of each eye opening toward the nose-piece 25. This serves to restrict the opening space outwardly of the members 22 and 23 to a circular area of diameter less than that of the game ball. Even though a handball, racquet ball and squash ball are relatively small, the goggles shown in FIGS. 4 and 5 provide excellent protection for the wearer and yet the visibility is maintained substantially unimpaired by the frame and obstruction members. Moreover, the collective effect of having a plurality of deflection points is also achieved in this version.

As a further aspect, another obstruction and deflection member 27 can be provided on the nose-piece at a position slightly above eye level, as shown in dashed-line depiction. With the addition of the further member, both members 24 and 27 may be of lesser extent into the viewing region of the opening 21, 21'.

Figure 6:
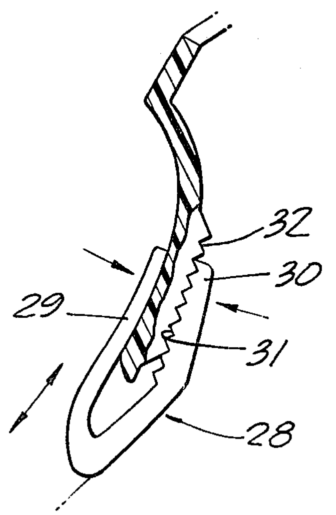
FIG. 6 is a sectional view of a nose-piece for use with the goggles of either of the embodiments.

FIG. 6 shows an adjustable nose-piece construction which may be used with either of the described embodiments. A resilient U-shaped member 28 has one smooth-surfaced arm 29 and a second arm 30 with serrations 31 on its inner surface. In use, the U-shaped member is slipped onto the nose-piece from underneath with the serrations 31 interlocking with a matching set of serrations 32 on the nose-piece. The outer surface of the member 28 facing the wearer is contoured to fit against the nose. Adjustment is achieved by spreading the arms 29 and 30 apart and positioning the member 28 at the correct height, after which, on releasing finger pressure, the mating of the serrations maintain the new position.

Although other means may be found acceptable, it is contemplated in both versions that the goggles will be secured onto the wearer by an elastic strap 33 in a conventional manner.

I claim:

1. Sport safety goggles, comprising:

frame means for being worn on the face of a sport participant, including first frame parts contacting the nose and the temple regions of the wearer and second frame parts defining first and second openings located respectively opposite the eyes of the wearer;

first and second elongated members extending generally vertically from top and bottom portions of the second frame parts into the opening defined by said frame parts;

third and fourth elongated members affixed to the first frame temple region parts and extending generally horizontally into the respective first and second openings; and fifth and sixth elongated members affixed to the first frame parts contacting the nose and extending respectively into the first and second openings;

all portions of the members extending into said first and second openings being free of contact of each other and the frame parts other than those parts at which they are affixed to said frame parts.

* * * * *